(12) United States Patent
Serra et al.

(10) Patent No.: US 7,377,182 B2
(45) Date of Patent: May 27, 2008

(54) MODULAR IMPLANT ASSEMBLY TOOL

(76) Inventors: Michael A. Serra, 4607 Hillwood Dr., Shingle Springs, CA (US) 95682; Alfred S. Despres, 4607 Hillwood Dr., Shingle Springs, CA (US) 95682

( * ) Notice: Subject to any disclaimer, the term of this patent is extended or adjusted under 35 U.S.C. 154(b) by 0 days.

(21) Appl. No.: 11/088,571

(22) Filed: Mar. 22, 2005

(65) Prior Publication Data

US 2006/0027027 A1   Feb. 9, 2006

Related U.S. Application Data

(63) Continuation of application No. 10/434,912, filed on May 9, 2003, now Pat. No. 6,871,549.

(60) Provisional application No. 60/378,974, filed on May 9, 2002.

(51) Int. Cl.
*G01N 3/08* (2006.01)

(52) U.S. Cl. ........................................... 73/819

(58) Field of Classification Search ... 73/862.392–393, 73/161, 819
See application file for complete search history.

(56) References Cited

U.S. PATENT DOCUMENTS

| | | | | |
|---|---|---|---|---|
| 4,026,161 A | * | 5/1977 | Vogel | ........................ 474/19 |
| 4,114,433 A | * | 9/1978 | Bowen | .................... 73/862.21 |
| 4,342,199 A | * | 8/1982 | Shaw et al. | .................. 62/133 |
| 4,439,926 A | * | 4/1984 | Whitney et al. | ............ 267/150 |
| 4,673,063 A | | 6/1987 | Engle | |
| 4,730,995 A | * | 3/1988 | Dewhirst | ........................ 418/1 |
| 4,820,283 A | * | 4/1989 | Schickling et al. | ......... 604/534 |
| 4,955,467 A | * | 9/1990 | Kallenbach | ................ 188/381 |
| 5,158,096 A | * | 10/1992 | Clark et al. | ................ 600/590 |
| 5,172,889 A | * | 12/1992 | Post et al. | ................. 254/10.5 |
| 5,362,929 A | | 11/1994 | Goto | |
| 5,410,920 A | | 5/1995 | Westwick | |
| 5,563,355 A | * | 10/1996 | Pluta et al. | ............ 73/862.625 |
| 6,036,694 A | | 3/2000 | Goble et al. | |
| 6,073,496 A | * | 6/2000 | Kuhn et al. | ............. 73/862.56 |
| 6,178,829 B1 | | 1/2001 | Ferguson | |
| 6,238,435 B1 | | 5/2001 | Meulink et al. | |
| 6,286,358 B1 | * | 9/2001 | Beetz et al. | ............. 72/409.12 |
| 6,536,263 B1 | | 3/2003 | Wood et al. | |
| 6,647,802 B2 | * | 11/2003 | Willson-Hackworth et al. | ........................... 73/826 |
| 6,871,549 B2 | * | 3/2005 | Serra et al. | ................... 73/819 |
| 6,901,818 B1 | * | 6/2005 | Cheung | ................ 73/862.393 |

* cited by examiner

*Primary Examiner*—Max Noori
(74) *Attorney, Agent, or Firm*—Pandiscio & Pandiscio

(57) ABSTRACT

This invention provides for a tool that produces, and directly and accurately measures, an axial force used to assemble two members of a modular implant, specifically, a modular hip implant.

5 Claims, 4 Drawing Sheets

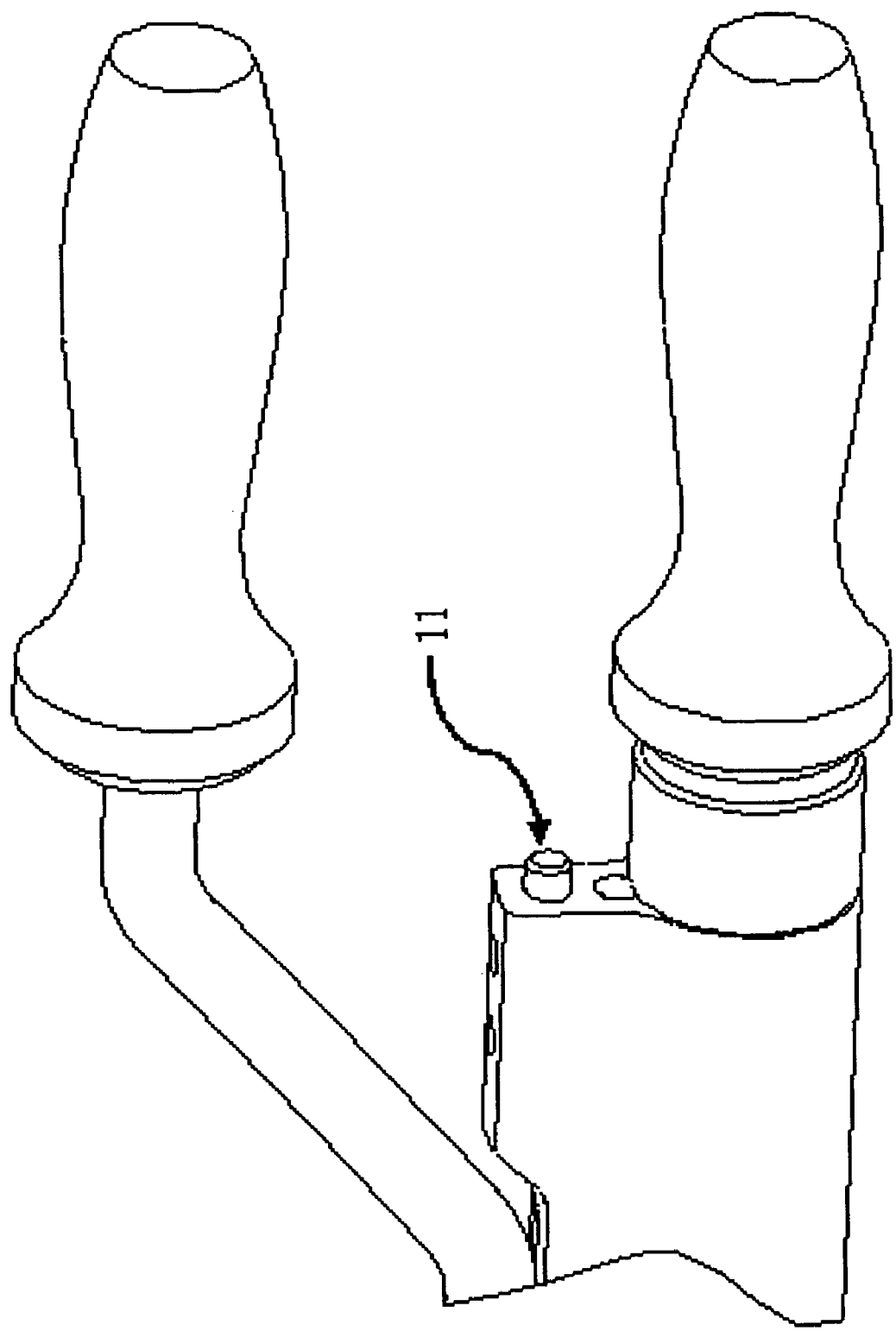

MODULAR IMPLANT ASSEMBLY TOOL

REFERENCE TO PENDING PRIOR PATENT APPLICATION

This is a continuation of prior U.S. patent application Ser. No. 10/434,912, filed May 9, 2003 now U.S. Pat. No. 6,871,594 by Michael A. Serra et al. for MODULAR IMPLANT ASSEMBLY TOOL, which in turn claims benefit of prior U.S. patent application Ser. No. 60/378,974, filed May 9, 2002 by Michael A. Serra et al. for DIRECT TENSION MEASURING IMPLANT ASSEMBLY TOOL.

The above-identified patent applications are hereby incorporated herein by reference.

FIELD OF THE INVENTION

This invention relates to medical apparatus and procedures in general, and more particularly to medical apparatus and procedures relating to total hip joints.

BACKGROUND OF THE INVENTION

Modular orthopedic implants are implants that comprise multiple components that are assembled at the time of surgery. In the case of a modular hip prosthesis, there may be separate stem, body, and neck segments. These orthopedic devices often use a self-locking taper to join the multiple components of the implant together. These tapers provide a strong frictional joint that resists the torsional loads seen in the implant. Due to the frictional nature of these locking tapers, large assembly loads are generally needed to completely and securely join the components. However, if the assembly loads are too large, detrimental stresses may be applied to the implant which may result in premature failure.

Prior assembly approaches commonly used impaction type devices, such as a hammer, to provide impulse loading to assemble the implants. While these approaches can be effective, they are also inconsistent. Factors such as hammer weight, the number of blows, and surgical technique can lead to assembly loads that are either too low (so that they result in ineffective locking) or too large (so that they impart undesirably large stresses in the parts), either of which may result in premature implant failure. In addition, in some cases where the patient's bone quality is poor, aggressive impactions can lead to fractures of the bone and poor surgical outcomes. Poor bone quality may also lead to under-assembled components because a large frictional interface is generally needed between the bone and the implant in order to produce enough resistance to fully assemble the components. Due to these concerns, alternate approaches for assembling these modular implants are needed.

Some current assembly approaches provide for an instrument that, through simple mechanical advantage, produces quasistatic opposing axial forces that assemble the implant without impact. Opposing axial force devices are commonly used in other applications such as hand riveting tools and manufacturing center tool spindles and tool collet holders. With these instruments it is important that the force being applied be measurable, accurate, and reproducible. Prior attempts at doing this, such as is disclosed in U.S. Pat. No. 6,238,435, typically use a design that measures the deflection of a beam subjected to an input load to calculate the axial tension generated. However, this approach generally lacks sufficient accuracy due to the change in mechanical advantage that occurs as the handles are brought together. More particularly, if the handles start far apart, the same force applied to the handle will produce a much smaller axial force than if the same force were applied with the handles close together. Other factors, such as where the surgeon applies the closing force along the length of the handle, will produce dramatically different axial forces as well.

The device as disclosed in U.S. Pat. No. 6,238,435, has a significant disadvantage when compared to an object of the present invention, when considering the indication of force. In U.S. Pat. No. 6,238,435, the force indicated is a function of the force applied to the handles. Because the force applied to the taper junction is a cosine function of the force applied to the handles, the surgeon is unable to detect or measure the force applied directly to the taper junction. It is an object of the present invention to give the surgeon a direct indication and measurement of the force applied to drawing the tapers together. As the spring element is compressed, the surgeon can see the amount of compression, and this compression is a direct and linear measurement of the amount of force applied directly to the taper junction.

The device as disclosed in U.S. Pat. No. 6,238,435, has a significant further disadvantage when compared to an object of the present invention, when considering the surgeon's perspective of the force applied to the handles, the angle between the handles, and the force applied to drawing the tapers together. In both devices, the force applied to the handles is very low prior to the engagement of the taper junction. However, once the taper junction is drawn together, using the device as disclosed in U.S. Pat. No. 6,238,435, the angle between the handles cannot be changed regardless of the force applied to the handles. In this "go/no go" situation, it is the surgeon's perspective that the handles move freely and then suddenly stop, the only additional motion detected by the surgeon is the bending deformation of the instrument itself.

It is an object of the present invention to give the surgeon greater visual and tactile feedback as a function of the applied drawing force once the taper is closed. Using the spring, or other element which has a change in length that is proportional to the applied force, once the taper is closed, the surgeon will continue to change the angle between the handles, which changes the length of the spring element, and thereby increases the force applied to the taper junction. This visual and tactile feedback allows the surgeon to finely adjust the amount of force applied to the taper junction.

No existing design directly measures the true axial force generated.

No existing design permits the generation of a predetermined axial force.

It is, therefore, an object of the present invention to provide a device for assembling modular implant components that directly indicates the assembly force applied to the components.

SUMMARY OF THE INVENTION

In view of the foregoing, there is provided a novel modular implant assembly tool formed in accordance with the present invention.

In one form of the present invention, there is provided an instrument for directly measuring an applied axial load, the instrument comprising: (a) two members that move coaxially in opposite directions with respect to one another; a first member being attached to the item to which the axial load is being applied, and a second member which is moved in the direction of the relevant axial load; (b) a spring body positioned between the two members; and (c) a scale including at least one indicia mark signifying the applied load or deflection of the spring body.

In another form of the present invention, there is provided an instrument for directly measuring an applied axial load, the instrument comprising: (a) two members that move coaxially in opposite directions with respect to one another, a first member being attached to the item to which the axial load is being applied, and a second member which is moved in the direction of the relevant axial load; (b) a spring body positioned between the two members, and (c) a mechanism which indicates when a predetermined force or displacement occurs in the spring body.

In another form of the present invention, there is provided an instrument for directly measuring an applied axial load, the instrument comprising: (a) two members that move coaxially in opposite directions with respect to one another, a first member being attached to the item to which the axial load is being applied, and a second member which is moved in the direction of the relevant axial load; (b) a piezoelectric element positioned between the first and second members; and (c) a device for converting the piezoelectric voltage into a signal indicating the force being applied to the piezoelectric element.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 4 is a schematic view showing an embodiment of the present invention that measures tension directly, using a button indicator.

DETAILED DESCRIPTION OF THE PREFERRED EMBODIMENTS

This invention improves upon existing designs by directly measuring, independently from input variables, the axial force generated while assembling modular implant components.

In a preferred embodiment of the present invention, this is accomplished by using a spring (or springs) to measure the true axial force being exerted. Springs deflect a predictable amount under load. If this deflection is measured and the spring rate is known, a force can be calculated.

In one embodiment this deflection can be measured using a scale. This scale may be labeled with force as the units. The scale may also represent a range of desirable loads. This range may be labeled with text, or color coded, to indicate adequate or inadequate assembly loads.

In another embodiment of the present invention, the required spring deflection may activate a trigger that alerts the user that the desired load has been reached. This trigger may release a button, make a sound, switch on a light or provide some other means of indication.

In another embodiment of the present invention, the force may be measured by a piezoelectric element whose voltage can be calibrated to a load. This voltage can be communicated to a user by means of a scale, light, sound, sensation (e.g. shock), etc.

Figure 1:
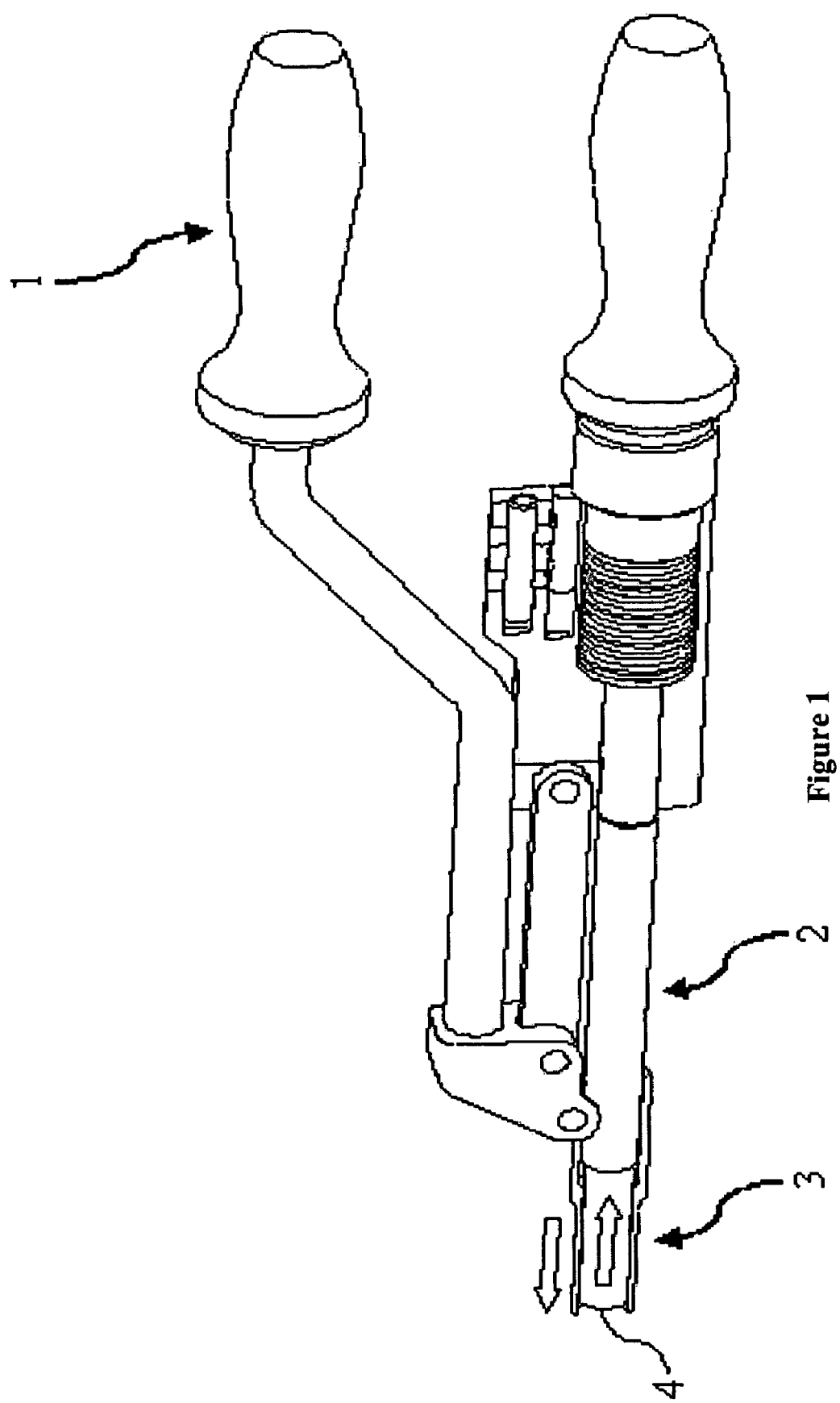
FIG. 1 is a schematic view showing an instrument which comprises a preferred embodiment of the present invention.

FIG. 1 shows an implant assembly tool formed in accordance with the present invention. Some sections of the tool have been cut away in FIG. 1 for clarity. By closing handles 1, shaft 2 is drawn up away from nose 3. This applies the assembly forces for the modular device attached at location 4.

Figure 2:
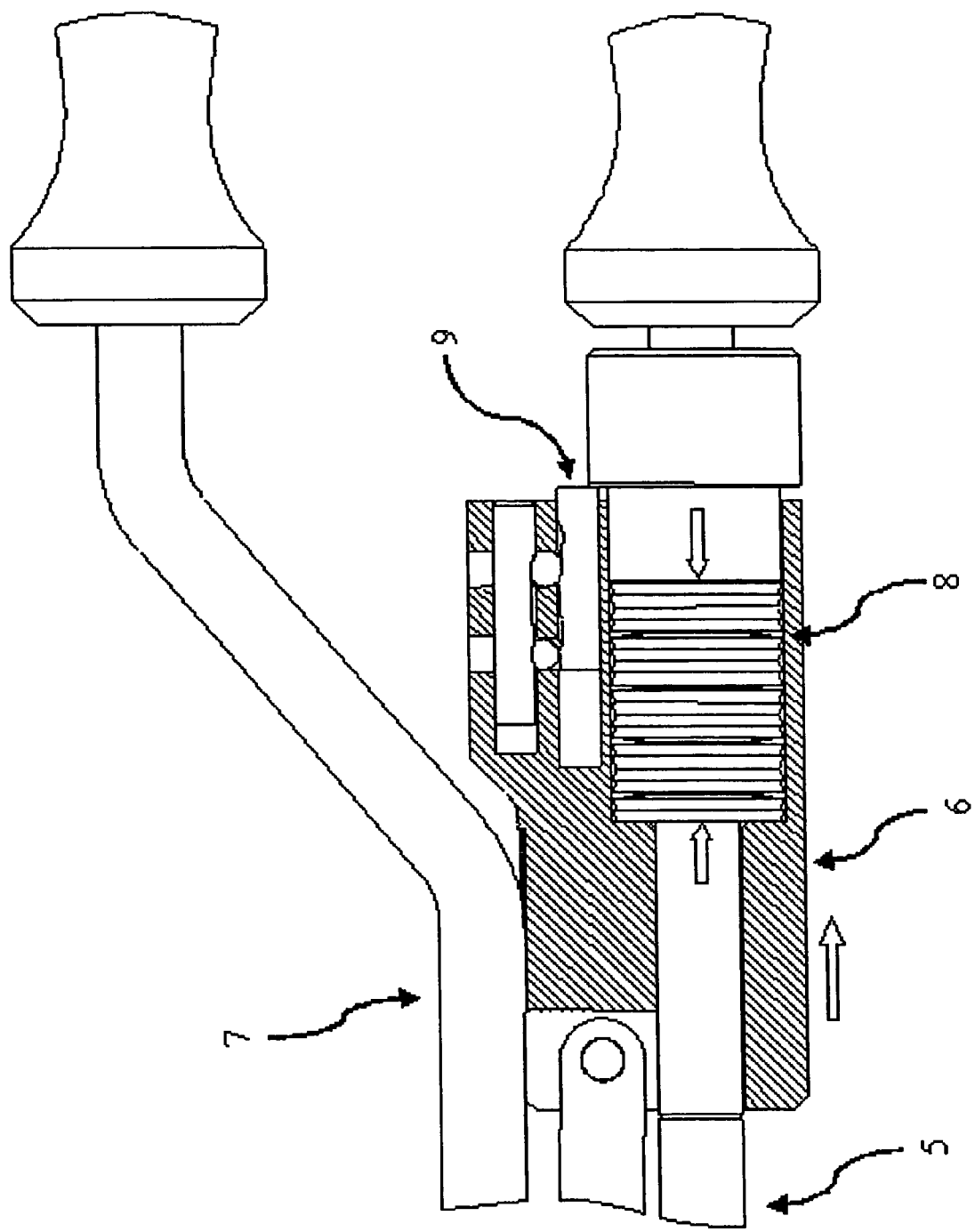
FIG. 2 is a schematic view showing an embodiment of the present invention using a spring to measure direct axial tension.

FIG. 2 shows an embodiment using springs to measure direct axial tension. Shaft 5 is attached to the implant. Housing 6, is attached to handle 7 by means of a mechanical linkage. Elements 5 and 6 move in opposite directions with respect to one another. The motion causes compression on spring(s) 8. In this embodiment the spring deflection is measured in a discrete amount by a triggering mechanism 9.

Figure 3:
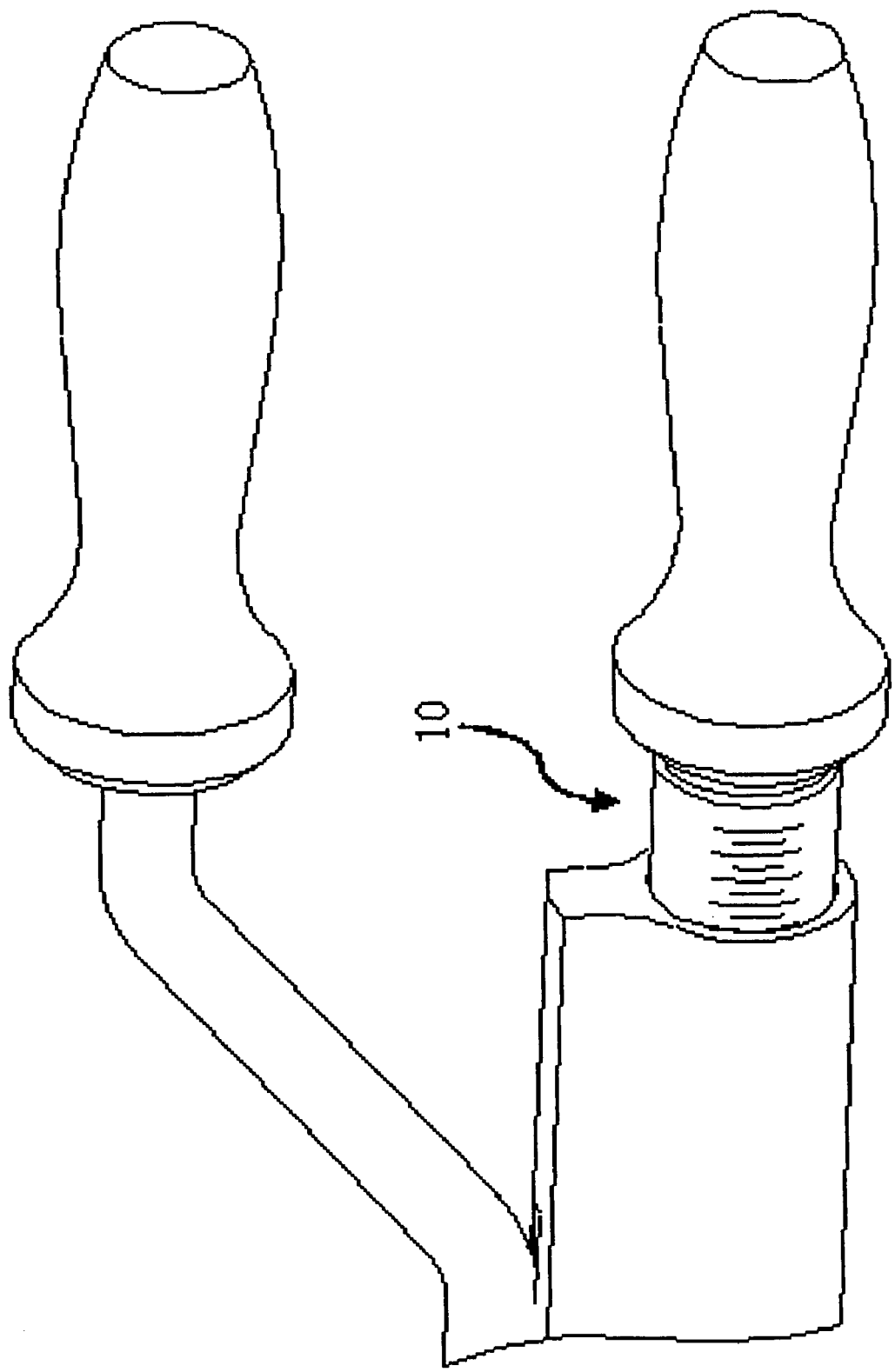
FIG. 3 is a schematic view showing an embodiment of the present invention that measures tension incrementally, using a scale.

FIG. 3 shows an embodiment of the present invention that measures tension incrementally, using a scale 10.

FIG. 4 shows an embodiment of the present invention that measure tension discretely, using a button indicator 11.

Still other embodiments of the present invention will be apparent to those skilled in the art in view of the present disclosure, and are considered to be within the scope of the present invention.

What is claimed is:

1. An instrument for measuring an applied axial load, the instrument comprising:
    first and second handles disposed side by side in parallel;
    a shaft extending from a distal end of said first handle;
    a housing mounted on said shaft, said shaft being axially slidable in said housing;
    a spring body disposed in said housing and positioned between said shaft and a portion of said housing;
    an indicator mounted on said housing and adapted to indicate applied axial load;
    said second handle being pivotally mounted on said shaft and being pivotally attached to said housing and operative to activate said indicator.

2. The instrument in accordance with claim 1, wherein said indicator comprises a piezoelectric element positioned between said shaft and at least a portion of said housing; and
    a device for converting piezoelectric voltage into a signal indicating force being applied to said piezoelectric element.

3. The instrument in accordance with claim 1 wherein said indicator comprises a scale mechanism adapted to indicate when a predetermined axial load occurs in the spring body.

4. An instrument for measuring an applied axial load, the instrument comprising:
    first and second handles disposed side by side in parallel;
    a shaft extending from a distal end of said first handle;
    a housing mounted on said shaft, said shaft being axially slidable in said housing;
    a spring body disposed in said housing and positioned between said shaft and a portion of said housing;
    an indicator mounted on said housing and adapted to indicate applied axial load;
    said second handle being pivotally mounted on said shaft and being pivotally attached to said housing and operative to activate said indicator;
    wherein said spring body comprises at least one coil spring.

5. An instrument for measuring an applied axial load, the instrument comprising:
    first and second handles disposed side by side in parallel;
    a shaft extending from a distal end of said first handle;
    a housing mounted on said shaft, said shaft being axially slidable in said housing;
    a spring body disposed in said housing and positioned between said shaft and a portion of said housing;
    an indicator mounted on said housing and adapted to indicate applied axial load;
    said second handle being pivotally mounted on said shaft and being pivotally attached to said housing and operative to activate said indicator;
    wherein said indicator comprises a button indicator.

* * * * *